(12) United States Patent
Jarrell et al.

(10) Patent No.: US 8,641,882 B2
(45) Date of Patent: Feb. 4, 2014

(54) CAPILLARY COLUMN CARTRIDGE

(75) Inventors: Joseph A. Jarrell, Newton Highlands, MA (US); Keith Edward Fadgen, Hope Valley, RI (US)

(73) Assignee: Waters Technologies Corporation, Milford, MA (US)

( * ) Notice: Subject to any disclaimer, the term of this patent is extended or adjusted under 35 U.S.C. 154(b) by 273 days.

(21) Appl. No.: 13/163,818

(22) Filed: Jun. 20, 2011

(65) Prior Publication Data

US 2012/0160690 A1    Jun. 28, 2012

Related U.S. Application Data

(60) Provisional application No. 61/359,590, filed on Jun. 29, 2010.

(51) Int. Cl.
*G01N 27/453* (2006.01)
*G01N 30/02* (2006.01)

(52) U.S. Cl.
USPC .............. 204/601; 422/70; 422/89; 73/61.52; 73/61.53

(58) Field of Classification Search
USPC .............. 422/70, 89; 73/61.52, 61.56, 61.61; 204/601–605, 451–455
See application file for complete search history.

(56) References Cited

U.S. PATENT DOCUMENTS

| | | | | |
|---|---|---|---|---|
| 5,198,091 | A * | 3/1993 | Burolla et al. | 204/601 |
| 6,613,224 | B1 * | 9/2003 | Strand | 210/198.2 |
| 7,473,342 | B2 * | 1/2009 | Ugai et al. | 204/601 |

OTHER PUBLICATIONS

Tanuja Koppal, "Liquid Chromatography Columns," Lab Manager Magazine®, Feb. 23, 2009, downloaded Jul. 16, 2013.*

* cited by examiner

*Primary Examiner* — Alex Noguerola
(74) *Attorney, Agent, or Firm* — Schmeiser, Olsen & Watts, LLP

(57) ABSTRACT

Described is a capillary column cartridge. The cartridge can be used to perform separations according to various techniques such as capillary gas chromatography, capillary electrophoresis and capillary liquid chromatography. The cartridge includes a capillary column secured in a cartridge body. The capillary column includes an inlet port and an outlet port that, in some embodiments, are disposed on a planar surface of the body. When the body is engaged to a separation system module, the inlet port is aligned to receive a sample to be separated and the outlet port is aligned to provide the separated sample to the separation system module. The path of the capillary through the body has a non-planar path shape such as a coil shape. Consequently, longer column lengths can be accommodated, leading to an improvement in separation resolution. The body can include a material having a high thermal conductivity to achieve improved thermal performance.

23 Claims, 3 Drawing Sheets

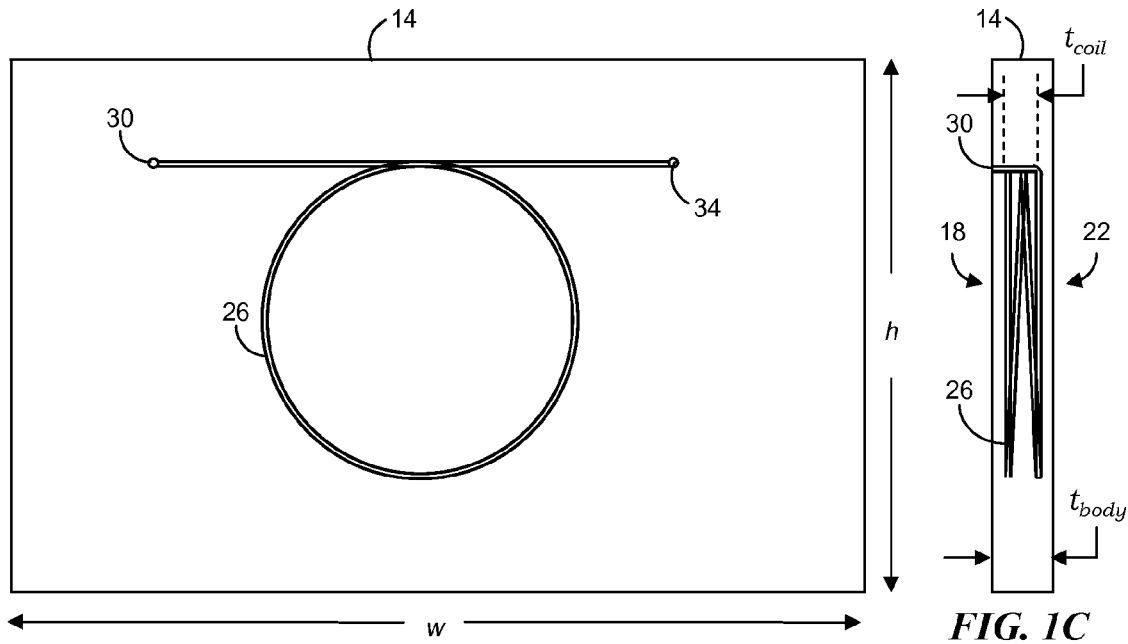
FIG. 1B
FIG. 1C
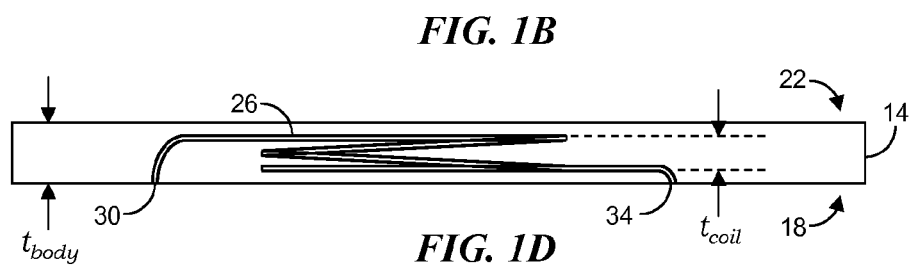
FIG. 1D
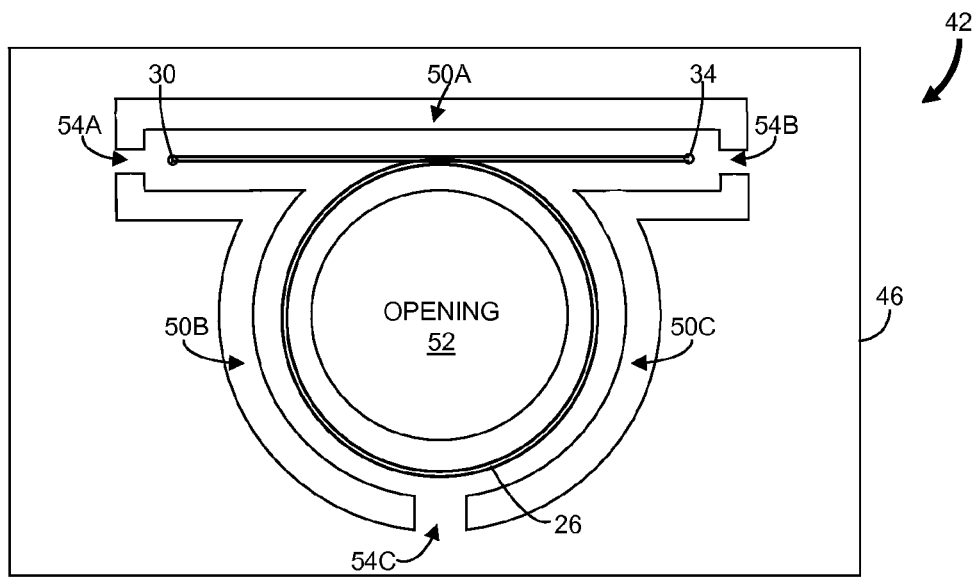
FIG. 3

CAPILLARY COLUMN CARTRIDGE

RELATED APPLICATION

This application claims the benefit of the earlier filing date of U.S. Provisional Patent Application Ser. No. 61/359,590, filed Jun. 29, 2010 and titled "Capillary Column Cartridge," the entirety of which is incorporated herein by reference.

FIELD OF THE INVENTION

The invention relates generally to columns used to perform separations. More particularly, the invention relates to a cartridge column for gas chromatography, capillary electrophoresis and capillary liquid chromatography systems that provides for improved thermal control and easy connection to other components of a chromatographic instrument.

BACKGROUND

Columns for capillary gas chromatography (GC), capillary electrophoresis (CE) and capillary liquid chromatography (CLC) typically use fused silica tubing coated with a polyimide. In these separation techniques, the tubing, or column, is replaced periodically due to aging or to permit a different separation to be performed. Fittings are used to couple the tubing to other components in the chromatography or CE system. The process of connecting or disconnecting the column can consume significant time and, if not properly performed, can degrade separation performance.

Accurate control of the column temperature is required to maintain performance of the separation. For CLC and CE systems, significant heat that may be generated in the column needs to be efficiently removed. Moreover, in GC systems, the temperature of the column is ramped precisely and repeatedly during a separation.

The present invention addresses the need for a device that provides an improvement in column connection and accurate temperature control of the column without adversely affecting the separation performance.

SUMMARY

In one aspect, the invention features a capillary column cartridge that includes a cartridge body and a capillary secured inside the cartridge body. The cartridge body has a planar surface and is configured to engage a separation system module. The capillary has an inlet port and an outlet port disposed on the planar surface, and a non-planar path through the cartridge body. When the cartridge body is engaged to the separation system module, the inlet port is aligned to receive a sample to be separated and the outlet port is aligned to provide the separated sample to the separation system module.

In another aspect, the invention features a capillary column cartridge that includes a cartridge body having a pair of surfaces and a body extension with an opening in the extension. The cartridge body is configured to engage a separation system module. The capillary column cartridge also includes a capillary that has an inlet port and an outlet port. The capillary has a non-planar path between the pair of surfaces and extends through the body extension. When the cartridge body is engaged to the separation system module, the inlet port is aligned to receive a sample to be separated and the outlet port is aligned to provide the separated sample to the separation system module. Access to the capillary at a location proximate to the outlet port is provided by the opening in the body extension.

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

FIG. 1A to FIG. 1D are various views of an embodiment of a capillary column cartridge according to the invention.

FIG. 3 illustrates another embodiment of a capillary column cartridge according to the invention.

DETAILED DESCRIPTION

Figure 1A:
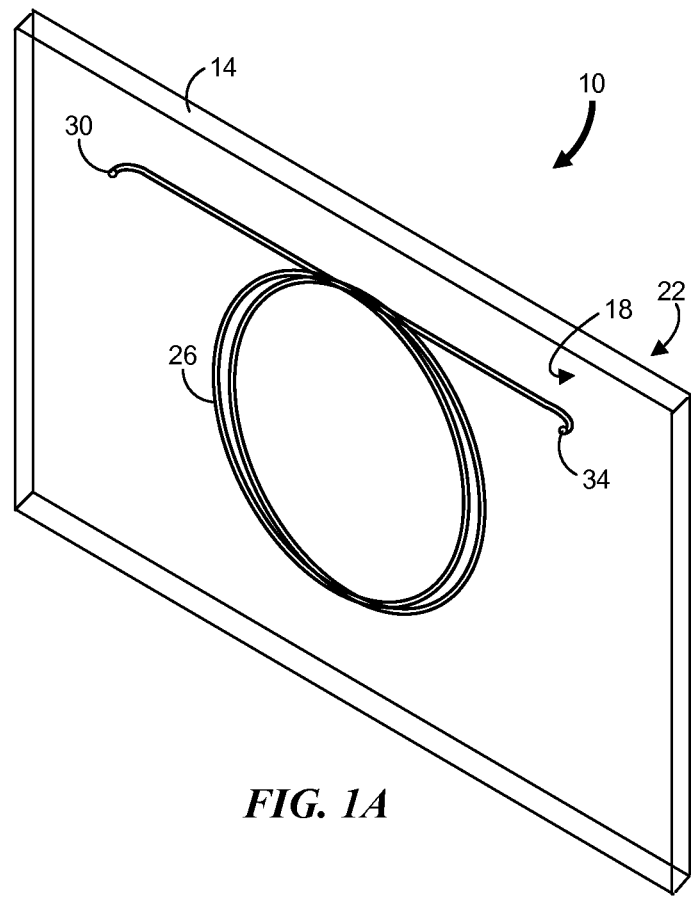

Reference in the specification to "one embodiment" or "an embodiment" means that a particular, feature, structure or characteristic described in connection with the embodiment is included in at least one embodiment of the teaching. The appearances of the phrase "in one embodiment" in various places in the specification are not necessarily all referring to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

Columns for capillary GC, capillary CE and CLC typically require replacement either on a periodic basis due to aging or to change the type of separation to be performed. Connecting and disconnecting the column can be time intensive and can adversely affect performance, for example, by introducing a dead volume at the coupling fittings. Moreover, accurate temperature control of the column is required and heat that is generated in the column may need to be removed. Various techniques have been developed to address these requirements. For example, ceramic tiles or polyimide sheets may be used to form a "lab on a chip" device in which the tiles or sheets are clamped between flat surfaces to effect connections and to enable accurate temperature control. Due to fabrication processes, the channels in such devices, which act as an equivalent to a capillary column, lie in a single plane. Thus there is a practical limit on the length of the separation channel in the device. The resolution of a separation is a function of the column length. Consequently, the resolution of a planar device is not adequate for many applications.

In brief overview, the invention relates to a cartridge having a capillary column. The cartridge can be used to perform separations according to various techniques such as capillary GC, capillary CE and CLC. The cartridge includes a capillary secured in a cartridge body. The capillary includes an inlet port and an outlet port that in some embodiments are disposed on a planar surface of the cartridge body. The path of the capillary through the cartridge body is in the shape of a coil or other non-planar path configuration. Consequently, longer column lengths are possible relative to lab on a chip devices, leading to an improvement in separation resolution.

The cartridge body is adapted for convenient coupling to a separation system module so that the inlet port is aligned to receive a sample to be separated from a sample source in the system module and the outlet port is aligned to provide the separated sample for detection to the system module. Advantageously, the cartridge is compact and can be inserted into and removed from the separation system module many times without adversely affecting performance. In preferred embodiments, the cartridge body is thermally-conductive so that the temperature of the capillary column can be accurately controlled. In some embodiments, the cartridge body includes a body extension having an opening. The capillary extends through the opening so that a portion of the capillary near the outlet port can be accessed. For example, an electrolyte well can be formed in the opening for a system configured to perform CE.

A capillary column cartridge 10 according to one embodiment of the invention is shown in an isometric view in FIG. 1A. A front, side and top view of the cartridge 10 are shown in FIG. 1B, FIG. 1C and FIG. 1D, respectively. The cartridge 10 is suitable for various GC and CLC applications. The cartridge 10 includes a cartridge body 14 having a thin planar structure that includes two planar parallel surfaces 18 and 22. A capillary column 26 is embedded inside the cartridge body 14.

Figure 2:
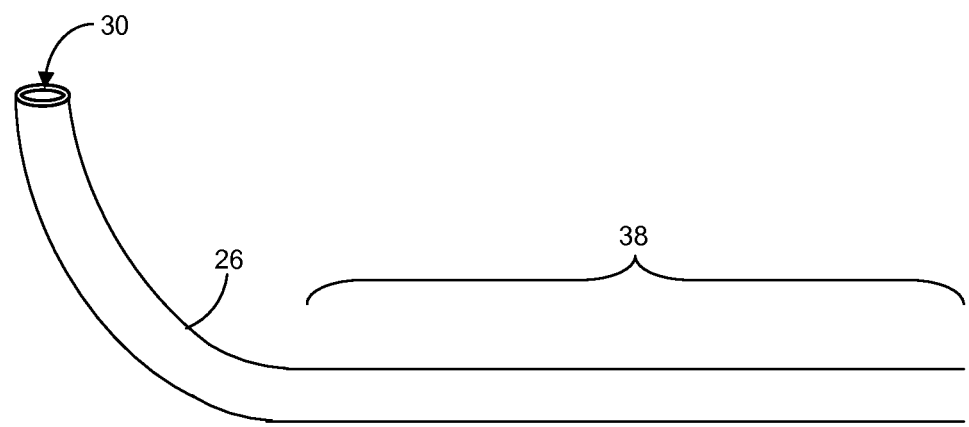
FIG. 2 is an illustration of a portion of the capillary column extending from the inlet port for the capillary column cartridge of FIG. 1.

The capillary 26 is in the form of a coil of fused silica tubing with a linear section extending from each end of the coil. As illustrated, the coil includes only two coil loops for clarity although the coil can include any number of overlapping loops to obtain the desired capillary column length. In some embodiments, the capillary 26 has a polyimide cladding. The capillary 26 has an inlet port 30 and an outlet port 34 that are flush with the front surface 18. FIG. 2 shows how the capillary 26 is gradually bent upward from the linear section 38 that lies parallel to the front surface (not shown) so that the inlet port is disposed on the front surface. The opposite end of the capillary is similarly configured so that the outlet port is also disposed on the front surface.

Referring again to FIG. 1A to FIG. 1D, the length of the capillary 26 can be long relative to the dimensions of the cartridge body 14. For example, the capillary 26 can be tens of meters long for GC separations while the width w and height h of the cartridge body 14 can be a few inches or less. In some embodiments, the coil thickness tcoil is determined by the capillary length used to obtain the desired separation resolution thus the cartridge body thickness tbody is generally greater for GC applications. Preferably the body thickness tbody 14 is not much greater than the coil thickness tcoil to maintain a low thermal mass for the cartridge 10 and thereby enable more accurate and rapid temperature control.

In other embodiments, the capillary 26 is configured with a different path shape. In general, the capillary 26 can be configured in any non-planar path that is accommodated by the dimensions of the cartridge body 14 and the minimum bend radius of the capillary 26. For example, the linear sections 38 may be reduced in length or eliminated and rather than a coil, the capillary can be formed into a spiral. The spiral configuration can be the equivalent of more than one coil, yet potentially have a thickness tcoil that is only the external diameter of the capillary. Alternately, the capillary can be configured as an array of zig-zag loops.

The cartridge body 14 can be fabricated from a number of materials. By way of examples, the body 14 may be formed from a polymer (e.g., polyether ether ketone (PEEK)) or a castable ceramic. In preferred embodiments, the body material is a thermally conductive matrix such as an epoxy impregnated with copper particles or boron nitride particles. The body 14 can have one or more registration features or marks used to align the capillary column cartridge 10 to a separation system module such as a GC system module or LC system module. Preferably the separation system module includes a registration mechanism to maintain a desired position of the cartridge 10 with respect to features in the separation system module that provide the sample to the inlet port 30 and receive the separated sample from the outlet port 34. In one embodiment, the registration mechanism includes a spring loaded mechanism to maintain the front surface 18 in a desired position with sufficient force to seal the ports 30 and 34 against the respective channels in the separation system module.

The capillary column cartridge 10 can be fabricated in a variety of ways. In a preferred technique, the capillary 26 is embedded, or encapsulated, in the cartridge body 14, for example, by using a casting or molding process. Alternatively, the capillary 26 can be inserted into a receiving region of a body structure. The receiving region is preformed, cut or ground to closely match the shape of the capillary path. A second body structure such as a plate or a complementary mating structure is attached to the first body structure to secure and enclose the capillary 26.

During fabrication, the ends of the capillary 26 extend through the front surface 18 of the cartridge body 14 at predetermined locations. The front surface 18 is polished so that the inlet and outlet ports 30 and 34 of the capillary 26 are formed to be flush with the front surface 18. In effect, the ports 30 and 34 appear as holes in the front surface 18. The tolerance on the port locations at the surface 18 is selected to ensure accurate alignment with channel ports in the separation system module that provide the sample and receive the separated sample. By way of example, the tolerance on the locations of the inlet port 30 and outlet port 34 on the front surface 18 can be 0.0005 in. for a 350 μm diameter capillary.

The cartridge 10 enables the inlet and outlet ports 30 and 34 to be connected to the corresponding fluid ports in a separation system module without the need for coupling fittings. Thus the time necessary for insertion and removal of the capillary 26 are substantially reduced in comparison to conventional capillaries. The inlet port 30 and outlet port 40 are sealed to corresponding features in the separation system module by applying a force to hold the planar surface of the cartridge 10 against a planar surface of the separation system having similar features to allow fluid or gas to enter and flow through the capillary 26. The actual force required to maintain a seal is based on the available sealing surface area and the fluid or gas pressure. The capillary column cartridge 10 is suitable for CLC applications in which the fluid can be at high pressures, for example, from 10,000 psi to 15,000 psi. By way of a specific example, the sealing force for a CLC application operating at 15,000 psi and having a sealing surface area of 0.010 square inches exceeds 150 lbs. of force. Less force is required for systems operating at lower pressures and/or having smaller sealing surface areas.

In some applications, the temperature of the capillary column needs to be varied rapidly and accurately. FIG. 3 illustrates another embodiment of a capillary column cartridge 42 that has a reduced thermal mass compared to the cartridge 10 of FIG. 1. The cartridge body 46 includes openings 50A to 50C (generally 50) that thermally isolate a first body region surrounding the capillary path from a second body region that includes most of the remaining region of the cartridge body 46. In addition, a circular opening 52 reduces the thermal mass of the region inside the coil path. Only three small support regions, or "bridges," 54A to 54C (generally 54) couple the mass of the first body region to the mass of the second body region. Consequently, the thermal conductivity between the two body regions is substantially limited. The illustrated embodiment is particularly useful for GC applications because the temperature of the capillary 26 can be increased and decreased faster than is possible using the cartridge 10 of FIG. 1. The cartridge 42 has the additional benefit of reducing the requirements on heating and cooling sources.

In alternative embodiments, the number and shape of the openings 50 and the number and shape of the supports 54 can vary. For example, a different configuration of openings 50 and supports 54 may be required to avoid interference with a particular capillary path.

Preferably, at least one of the surfaces in the separation system module that receives the cartridge 42 is configured to apply heat to or conduct heat from the body region surrounding the capillary 26. In a preferred embodiment, the cartridge body 46 is selectively doped for improved thermal performance. More specifically, the body region surrounding the capillary 26 is doped, or embedded, with metal or other material having a high thermal conductivity. Optionally, a thermal insulator material is used in the support regions 54 or the second body region.

Figure 4:
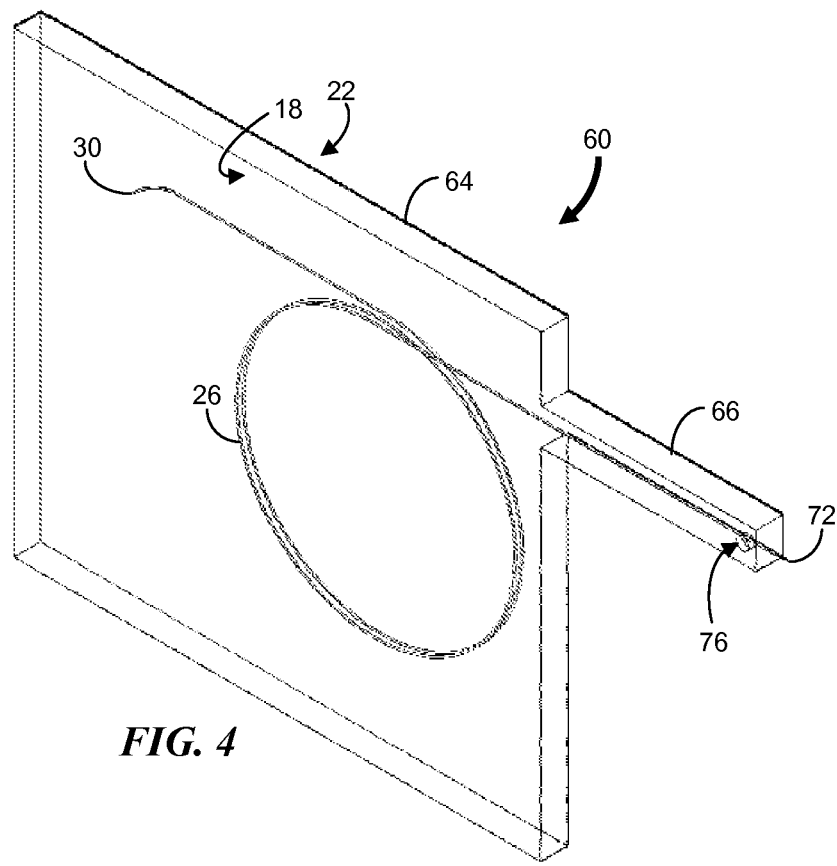
FIG. 4 illustrates another embodiment of a capillary column cartridge according to the invention.
Figure 5:
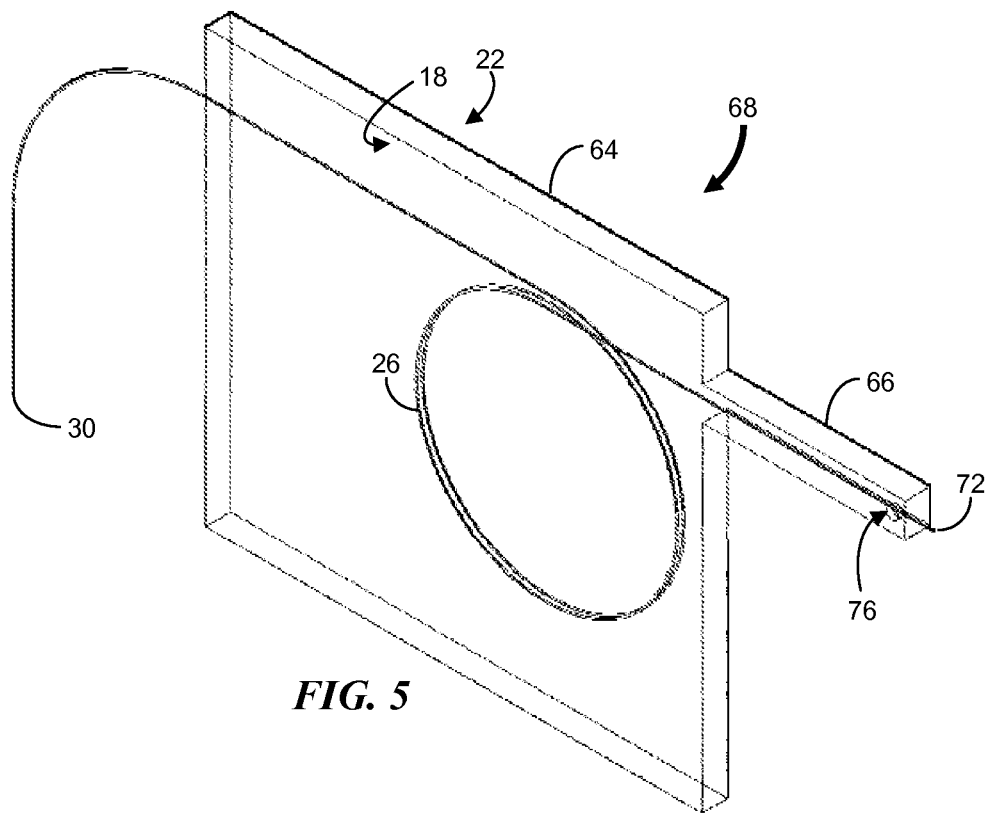
FIG. 5 illustrates another embodiment of a capillary column cartridge according to the invention.

In some applications, such as when interfacing with a mass spectrometer, it is advantageous to have an end portion of the capillary extend from the cartridge body. Alternatively, the outlet port of the capillary can abut a connection tube that extends outside the cartridge body. FIG. 4 shows an embodiment of a capillary column cartridge 60 that includes a cartridge body 64 having an extension 66 that surrounds a portion of a linear segment of the capillary 26. FIG. 5 shows an alternative embodiment of a capillary column cartridge 68 wherein a portion of the capillary 26 near the inlet port 30 extends outside the cartridge body 64. In both configurations, a connection tube at the output port of the capillary 26 includes an electrospray tip 72. A porous portion of the capillary 26 is exposed through an opening 76 in the extension 66. The opening 76 accommodates a well containing an electrolyte that provides an electrical coupling through the porous region to the fluid in the capillary 26. This configuration permits the application of a high voltage (e.g., 30,000 volts) to be applied across the length of the capillary path to enable CE separations to be performed. A similar configuration without the opening 76 and with an open end replacing electrospray tip 72 can be used to interface a GC capillary column to a mass spectrometer.

In some embodiments, additional or alternate openings are used, which can enable other measurements on the analytes passing through a capillary. For example, in the case of CLC or CE systems, such additional ports may be used to transilluminate the capillary so that analyte presence can be detected by the absorption of ultraviolet light, a standard measurement technique in conventional chromatography. In some instances these ports may contain optical elements such as lenses.

While the invention has been shown and described with reference to specific embodiments, it should be understood by those skilled in the art that various changes in form and detail may be made therein without departing from the spirit and scope of the invention as recited in the accompanying claims. For example, in various embodiments disclosed above the inlet and outlet ports of the capillary are on a surface having a large area relative to other surfaces of the cartridge body. The invention also contemplates that an inlet or outlet port can be present on one of the narrow surfaces of the cartridge body.

What is claimed is:

1. A capillary column cartridge, comprising:
a cartridge body having a planar surface and configured to engage a separation system module; and
a capillary embedded in the cartridge body and having an inlet port and an outlet port each disposed flush to the planar surface, the capillary having a non-planar path through the cartridge body, the inlet port and the outlet port being aligned to receive a sample to be separated and to provide the separated sample to the separation system module, respectively, when the cartridge body is engaged to the separation system module.

2. The capillary column cartridge of claim 1 wherein the non-planar path is a coil path.

3. The capillary column cartridge of claim 1 wherein the cartridge body comprises a thermally conductive material.

4. The capillary column cartridge of claim 1 wherein the capillary is embedded in the cartridge body by a casting process.

5. The capillary column cartridge of claim 1 wherein the cartridge body comprises at least one registration feature to align the capillary column cartridge to the separation system module.

6. The capillary column cartridge of claim 1 wherein the cartridge body comprises a first region that surrounds at least a portion of the path of the capillary and a second region separated from the first region by a plurality of openings to thereby reduce a thermal conductivity between the first and second regions.

7. The capillary column cartridge of claim 1 wherein the cartridge body comprises a plurality of body sections, at least one of the body sections having a channel therein to receive the capillary, the body sections being fixed to each other to secure the capillary within the cartridge body, at least one of the body sections having the planar surface with the inlet and outlet ports disposed therein.

8. The capillary column cartridge of claim 1 wherein the separation system module is a liquid chromatography system module.

9. The capillary column cartridge of claim 1 wherein the separation system module is a gas chromatography system module.

10. The capillary column cartridge of claim 1 wherein the separation system module is a capillary electrophoresis system module.

11. A capillary column cartridge, comprising:
a cartridge body having a pair of surfaces and a body extension with an opening therein, the cartridge body configured to engage a separation system module; and
a capillary embedded in the cartridge body and having an inlet port and an outlet port, the capillary having a non-planar path between the pair of surfaces and extending through the body extension, the inlet port and the outlet port being aligned to receive a sample to be separated and to provide the separated sample to the separation system module, respectively, when the cartridge body is engaged to the separation system module, wherein access to the capillary proximate to the outlet port is provided by the opening in the body extension.

12. The capillary column cartridge of claim 11 wherein the inlet port is disposed in one of the surfaces of the cartridge body.

13. The capillary column cartridge of claim 11 wherein the inlet port is external to the cartridge body.

14. The capillary column cartridge of claim 11 wherein the non-planar path is a coil path.

15. The capillary column cartridge of claim 11 wherein the cartridge body comprises a thermally conductive material.

16. The capillary column cartridge of claim 11 wherein the capillary is embedded in the cartridge body by a casting process.

17. The capillary column cartridge of claim 11 wherein the cartridge body comprises at least one registration feature to align the capillary column cartridge to the separation system module.

18. The capillary column cartridge of claim 11 wherein the cartridge body comprises a first region that surrounds at least a portion of the path of the capillary and a second region separated from the first region by a plurality of openings to thereby reduce a thermal conductivity between the first and second regions.

19. The capillary column cartridge of claim 11 wherein the cartridge body comprises a plurality of body sections, at least one of the body sections having a channel therein to receive the capillary, the body sections being fixed to each other to secure the capillary within the cartridge body, at least one of the body sections having the planar surface with the inlet and outlet ports disposed therein.

20. The capillary column cartridge of claim 11 wherein the separation system module is a liquid chromatography system module.

21. The capillary column cartridge of claim 11 wherein the separation system module is a gas chromatography system module.

22. The capillary column cartridge of claim 11 wherein the separation system module is a capillary electrophoresis system module.

23. The capillary column cartridge of claim 22 further comprising an electrolyte well disposed in the aperture and wherein the capillary comprises a porous region disposed in the electrolyte well.

* * * * *